United States Patent
Liang et al.

(10) Patent No.: US 11,524,060 B2
(45) Date of Patent: Dec. 13, 2022

(54) ATTENUATION SYSTEM AND USE THEREOF

(71) Applicant: GUANGZHOU CAS LAMVAC BIOTECH CO., LTD, Guangzhou (CN)

(72) Inventors: Xingxiang Liang, Guangzhou (CN); Jianhua Su, Guangzhou (CN); Meiling Wang, Guangzhou (CN); Ying Tong, Guangzhou (CN); Yongchao Yao, Guangzhou (CN); Li Qin, Guangzhou (CN); Xiaoping Chen, Guangzhou (CN)

(73) Assignee: GUANGZHOU CAS LAMVAC BIOTECH CO., LTD, Guangzhou (CN)

( * ) Notice: Subject to any disclaimer, the term of this patent is extended or adjusted under 35 U.S.C. 154(b) by 0 days.

(21) Appl. No.: 17/050,771

(22) PCT Filed: Apr. 26, 2018

(86) PCT No.: PCT/CN2018/084643
§ 371 (c)(1),
(2) Date: Jan. 31, 2021

(87) PCT Pub. No.: WO2019/205058
PCT Pub. Date: Oct. 31, 2019

(65) Prior Publication Data
US 2021/0145953 A1    May 20, 2021

(51) Int. Cl.
| C12P 21/06 | (2006.01) |
| A61K 39/015 | (2006.01) |
| A61P 33/06 | (2006.01) |
| C07K 14/445 | (2006.01) |
| C12N 1/36 | (2006.01) |
| C12N 15/79 | (2006.01) |
| A61K 39/00 | (2006.01) |

(52) U.S. Cl.
CPC ............ *A61K 39/015* (2013.01); *A61P 33/06* (2018.01); *C07K 14/445* (2013.01); *C12N 1/36* (2013.01); *C12N 15/79* (2013.01); *A61K 2039/522* (2013.01)

(58) Field of Classification Search
None
See application file for complete search history.

(56) References Cited

U.S. PATENT DOCUMENTS

2003/0040544 A1   2/2003  Jacobus et al.
2014/0154289 A1   6/2014  Vaquero et al.

FOREIGN PATENT DOCUMENTS

| CN | 102595894 A | 7/2012 |
| CN | 102776217 A | 11/2012 |
| CN | 103874506 A | 6/2014 |
| CN | 105695472 A | 6/2016 |
| CN | 106905247 A | 6/2017 |
| WO | 2017136556 A | 8/2017 |
| WO | 2018005873 A1 | 1/2018 |

OTHER PUBLICATIONS

Otto et al., "Plasmodium berghei ANKA elongation factor 1-gamma, putative (PBANKA_135200), partial mRNA", BMC Biol 12, 86 (2014).
Int'l Search Report (PCT/CN2018/084643), dated Jan. 25, 2019.
Plasmodium berghei ANKA elongation factor 1-gamma, putative (PBANKA_135200), partial mRNA, XM_022857911.1, GENBANK, Oct. 24, 2017.
Examination Report dated Feb. 23, 2022 for GB2017657.4.
PNAS vol. 108(11) 2011, Muralidharan et al., "Asparagine repeat function in a Plasmodium falciparum protein assessed via a regulatable fluorescent affinity tag" p. 4411-4416 available at URL https://www.pnas.org/doi/epdf/10.1073/pnas.101844910 See Results.
Examination Report dated Jul. 1, 2022 for GB2017657.4.
Nature Methods vol. 4, 2007, Armstrong et al., "An FKBP destabilization domain modulates protein levels in Plasmodium falciparum" See abstract available at https://www.nature.com/articles/nmethl 132.
Cell host and microbe, vol. 12, 2012, Pino et al., "A tetracycline-repressible transactivator system to study essential genes in malaria parasites" pp. 824-834 available at URL https://www.sciencedirect.com/science/article/pii/SI931312812003654 See Figure 2.

*Primary Examiner* — Jennifer E Graser
(74) *Attorney, Agent, or Firm* — Hunton Andrews Kurth LLP (57) ABSTRACT

Disclosed are an attenuation system and the use thereof for attenuating plasmodia, specifically the use of an EF1g gene for attenuating plasmodia. The attenuation system regulates the expression or degradation of the EF1g gene by using a regulatory system, thereby controlling the growth of plasmodia and achieving the attenuation of plasmodia.

6 Claims, 7 Drawing Sheets

Specification includes a Sequence Listing.

SEQUENCE LISTING

```
<160> NUMBER OF SEQ ID NOS: 7

<210> SEQ ID NO 1
<211> LENGTH: 1212
<212> TYPE: DNA
<213> ORGANISM: Plasmodium berghei

<400> SEQUENCE: 1
atggatttaa aacttcttgg cccaaaaaat gatatcagat gtttgaaggt gcaaacagtt      60
gcttcttttt gtaatataaa actaaatatc ccaacatttg aaatcggtat tgatgataat     120
aaagatgaat ttataaaaga atcgccaatg aaaagacttc cagttttaat aacaccccaa     180
ggaagcttat ttgaaagcaa tgctatagga aaatatttat gcagtataag aagtgaacat     240
aatttattgg gaaatggaat ttttgaagaa gggcaagtaa atatgtgggt agattttttgt    300 acatttgaat tagaaattcc agtatgctgt tatattagta ataagttgaa tgaaaaatcg     360
ttaaaacata ttcaagatac atttagttgt ttaaataaac acttactatt aaatcagtat     420
atggtaggta acaacataac tattgttgat attttttatgt ctgtaattat aaatttttgt   480
ataaaatcgg gaaaaatgac tgaagccttt ttaaaacaat atggaaactt atacagatta     540
tatacaacta taataaatca gaaacaattt aaatatgtta tgggttcagg atcagctgta    600
aataataaaa aaacacctac tcaacccaaa cagccaaata ataaggaaaa aaaaaaacca     660
aaagaagatg cagatgatga tattaatcta tttagtgatg atggacttaa tgaaaaaaaa    720
acaaaaaaga caaaccctttt agatttatta cctccatcaa aattttcttt agataactgg    780
aaatataaat ttagtaatga aaaggattta ttaaaaaatg caatgcccac attttgggaa    840
acttatgata gtaatggatt ttcattatat tatatgaaat atgataaatt agaagatgaa    900
tgccaaatat cttttgttgc ttgtaatatg gctagtgggt ttttacaaag gttagaaaac    960
aatttctcaa aatactcatt tgcagttata tctgttttag gggaaaataa aaattatgat   1020
attgaaggtg tttggctatt tagaggtact gaaattcctt ttgaaatgaa agaccatcca   1080
tcttttgaat atcacatttt taaaaaatta gatattaata acagtaatga taaaaaactt   1140
gttgaagatt attggtgttc aaaagaaatt atttctaata gacctgtttg tgatagaaag   1200
gtttggaaat ga                                                       1212

<210> SEQ ID NO 2
<211> LENGTH: 477
<212> TYPE: DNA
<213> ORGANISM: Artificial sequence
<220> FEATURE:
<223> OTHER INFORMATION: ecDHFR

<400> SEQUENCE: 2
atgatcagtc tgattgcggc gttagcggta gattatgtta tcggcatgga aaacgccatg     60
ccgtggaacc tgcctgccga tctcgcctgg tttaaacgca acaccttaaa taaacccgtg    120
attatgggcc gccataccctg ggaatcaatc ggtcgtccgt tgccaggacg caaaaatatt    180
```
atcctcagca gtcaaccggg tacggacgat cgcgtaacgt gggtgaagtc ggtggatgaa    240
gccatcgcgg cgtgtggtga cgtaccagaa atcatggtga ttggcggcgg tcgcgttatt    300
gaacagttct tgccaaaagc gcaaaaactg tatctgacgc atatcgacgc agaagtggaa    360
ggcgacaccc atttcccgga ttacgagccg atgactggga atcggtatt cagcgaattc    420 cacgatgctg atgcgcagaa ctctcacagc tattgctttg agattctgga gcggcgg       477

<210> SEQ ID NO 3
<211> LENGTH: 714
<212> TYPE: DNA
<213> ORGANISM: Artificial sequence
<220> FEATURE:
<223> OTHER INFORMATION: GFPm3

<400> SEQUENCE: 3
atgagtaaag gagaagaact tttcactgga gttgtcccaa ttcttgttga attagatggt     60
gatgttaatg ggcacaaatt ttctgtcagt ggagagggtg aaggtgatgc aacatacgga    120
aaacttaccc ttaaatttat ttgcactact ggaaaactac ctgttccatg gccaacactt    180
gtcactactt tcggttatgg tgttcaatgc tttgcgagat acccagatca tatgaaacag    240
catgactttt tcaagagtgc catgcccgaa ggttatgtac aggaaagaac tatattttc     300 aaagatgacg ggaactacaa gacacgtgct gaagtcaagt ttgaaggtga tacccttgtt    360
aatagaatcg agttaaaagg tattgatttt aaagaagatg gaaacattct tggacacaaa    420
ttggaataca actataactc acacaatgta tacatcatgg cagacaaaca aaagaatgga    480
atcaaagtta acttcaaaat tagacacaac attgaagatg gaagcgttca actagcagac    540
cattatcaac aaaatactcc aattggcgat ggccctgtcc ttttaccaga caaccattac    600
ctgtccacac aatctgccct ttcgaaagat cccaacgaaa agagagacca catggtcctt    660
cttgagtttg taacagctgc tgggattaca catggcatgg atgaactata caaa          714

<210> SEQ ID NO 4
<211> LENGTH: 750
<212> TYPE: DNA
<213> ORGANISM: Artificial sequence
<220> FEATURE:
<223> OTHER INFORMATION: EF1g homologous arm 1

<400> SEQUENCE: 4
actcctatag gcttaataat tataagcgct atatatatca catgcaactt aaaaaaaaat     60
atgcatatat ataattttc atgattgcaa aagaagttt gaatatttta aaaataaaa      120 cacattccaa ttatttgtcg ctaaatttta tttttaatta aatatatcgc acaaaagtat    180
aaacacatat agtattttc gtgttaataa ataacaata gttgaactac aaaacgaact     240
attttattag tcaattaatt taggatattt ttccttaaaa aaactaaata tatattatac    300 caaatattt ccatcataat tgtagattta cttttatt aaactaggga aatggattt       360 agtaagaaaa aaaaaaaaa aaaacatat atattgtatg ttctaaatat gtttataatt    420
tgagtaaata aaaataaaat ttcacataat atcagcaatg catagtataa aaaaaaaca    480 tcaaattaaa aatatatat tattatacaa tttaaaaaat gagcatacaa catttagttc    540
atgatatatg cataattata ttatatgttc ataaaataat ttttcttat tttttttct    600 taattttcat agaaacttct tggcccaaaa aatgatatca gatgtttgaa ggtgcaaaca    660
gttgcttctt tttgtaatat aaaactaaat atcccaacat ttgaaatcgg tattgatgat    720

```
aataaagatg aatttataaa agaatcgcca                                  750
```

<210> SEQ ID NO 5
<211> LENGTH: 741
<212> TYPE: DNA
<213> ORGANISM: Artificial sequence
<220> FEATURE:
<223> OTHER INFORMATION: EF1g homologous arm 2

<400> SEQUENCE: 5

```
aatgctatag gaaaatattt atgcagtata agaagtgaac ataatttatt gggaaatgga    60
atttttgaag aagggcaagt aaatatgtgg gtagattttt gtacatttga attagaaatt   120
ccagtatgct gttatattag taataagttg aatgaaaaat cgttaaaaca tattcaagat   180
acatttagtt gtttaaataa acacttacta ttaaatcagt atatggtagg taacaacata   240
actattgttg atatttttat gtctgtaatt ataaattttt gtataaaatc gggaaaaatg   300
actgaagcct ttttaaaaca atatggaaac ttatacagat tatatacaac tataataaat   360
cagaaacaat ttaaatatgt tatgggttca ggatcagctg taaataataa aaaaacacct   420
actcaaccca acagccaaa taataaggaa aaaaaaaaac caaagaaga tgcagatgat    480
gatattaatc tatttagtga tgatggactt aatgaaaaaa aaacaaaaaa gacaaaccct   540
ttagatttat tacctccatc aaaatttcct ttagataact ggaaatataa atttagtaat   600
gaaaaggatt tattaaaaaa tgcaatgccc acattttggg aaacttatga tagtaatgga   660
ttttcattat attatatgaa atatgataaa ttagaagatg aatgccaaat atcttttgtt   720
gcttgtaata tggctagtgg g                                           741
```

<210> SEQ ID NO 6
<211> LENGTH: 38
<212> TYPE: DNA
<213> ORGANISM: Artificial sequence
<220> FEATURE:
<223> OTHER INFORMATION: EF1-g-tar1-F

<400> SEQUENCE: 6

```
tattggagac gctttcaaat aagcttcctt gcgtctca                          38
```

<210> SEQ ID NO 7
<211> LENGTH: 38
<212> TYPE: DNA
<213> ORGANISM: Artificial sequence
<220> FEATURE:
<223> OTHER INFORMATION: EF1-g-tar1-R

<400> SEQUENCE: 7

```
aaactgagac gcaaggaagc ttatttgaaa gcgtctcc                          38
```

ATTENUATION SYSTEM AND USE THEREOF

TECHNICAL FIELD

The present disclosure relates to the field of genetic engineering and, in particular, to an attenuation system and use thereof, especially an attenuation system and use thereof for attenuating *Plasmodium*.

BACKGROUND

Malaria, AIDS, and tuberculosis are three major infectious diseases in the world. Malaria is an infectious disease caused by the single-celled protozoan *Plasmodium* and spread by *Anopheles* mosquitoes. The *Plasmodium* living inside human bodies is divided into four species: *P. falciparum, P. malariea, P. vivax,* and *P. ovale*. 95% of malaria deaths are caused by *P. falciparum* infection and mainly distributed in sub-Saharan Africa. Currently, the main animal models for malaria researches are mouse malaria models and monkey malaria models. *Plasmodium* for mouse can be divided into *P. chaubdi, P. berghei., P. yoelii,* and *P. vinckei*, etc. *Plasmodium* for monkey mainly includes *P. knowlesi* and *P. cynomolgi*.

Hosts of human *Plasmodium* include humans and *Anopheles* mosquitoes. Human *Plasmodium* will reproduce asexually in humans and reproduce sexually in *Anopheles* mosquitoes. Human *Plasmodium* undergoes two stages: a liver stage and an erythrocytic stage in the human body. In the liver stage, the *Plasmodium* undergoes schizogony to form merozoites. In the erythrocytic stage, the merozoites undergo schizogony, part of which form gametocytes which can sexually reproduce. Mature *Plasmodium* sporozoites exist in the salivary glands of *Anopheles* mosquitoes. When the *Anopheles* mosquito bites the human body, the sporozoites are injected into the human blood. Through blood circulation, the sporozoites invade hepatocytes and undergo schizogony in the hepatocytes within a few minutes. After the sporozoites develop for ten to twelve days and become mature, the hepatocytes are ruptured by a schizont which releases merozoites into the blood. Some merozoites continue to infect hepatocytes, some merozoites invade erythrocytes and enter the erythrocytic stage, and most of the remaining merozoites are swallowed by phagocytes. The merozoites that invade the erythrocytes continue to develop and go through the stages of rings, macrotrophozoites, immature schizonts, and mature schizonts. The mature schizonts overflow out of erythrocytes. In this stage, the schizonts will not invade the liver, and some schizonts can continue infecting erythrocytes. Some schizonts no longer divide after several times of schizogony and continue to develop into female or male gametocytes. A large number of *Plasmodium* gametocytes exist in the body of a malaria patient. When the *Anopheles* mosquito bites the malaria patient, the mature male and female gametocytes enter the mosquito's stomach and begin the sexual reproduction. The male and female gametocytes further develop into male and female gametes. The male and female gametes fuse into a zygote which further develops into an ookinete. The ookinete invades the stomach wall of the *Anopheles* mosquito to form an oocyst which undergoes asexual reproduction in the spore proliferation stage. The spores proliferate to form a large number of sporozoites free from the oocyst, and the sporozoites migrate to the salivary glands of the *Anopheles* mosquito and enter the next life cycle.

According to the latest estimates released by the World Health Organization in December 2016, there were 212 million malaria cases and 429,000 deaths in 2015. It was found from the statistics in 2015 that about half of the world's population was threatened by malaria which mainly occurred in the Sahara and South Africa and threatened people in Southeast Asia, Latin America, and the Middle East to different degrees. The malaria statistics in 2015 showed that malaria still continuously occurred in 91 countries and regions in the world, and malaria cases in sub-Saharan Africa accounted for 90% of global malaria cases and 92% of the total malaria deaths. Moreover, in these regions where malaria is highly spread, children under the age of 5 are very susceptible to malaria and get sick, and serious ones are even dead. More than 70% of malaria deaths happen to children under the age of 5, and one child dies of malaria every two minutes. Therefore, malaria is the first killer for the children under the age of 5. In addition to the children under the age of 5, infants, pregnant women, and AIDS patients with low immunity are all at a high risk of malaria.

Therefore, a highly effective malaria vaccine is of great significance for protecting humans and eliminating malaria. However, little progress has been made in vaccine research and development due to the complicated life cycle of *Plasmodium*, the variable components of antigens, and the imperfect experimental model of vaccine researches, etc. At present, malaria vaccines mainly include the following vaccines: 1. a pre-erythrocytic vaccine, such as RTS, which induces an antibody against circumsporozoite proteins and has relatively good clinical protection effects but low protectivity of only 25-50%, and other pre-erythrocytic subunit protein vaccines and DNA vaccines that have no obvious protective effect; 2. an erythrocytic vaccine that is developed using a merozoite surface antigen, an antigen involved in invading erythrocytes, and an infected erythrocyte surface antigen, among which erythrocytic subunit vaccines developed for MSP1 and AMA1 have no obvious protective effect; 3. a transmission-blocking vaccine that prevents the binding of gametocytes or the development of the zygote using gametocyte or zygote surface antigens so as to block the spread of malaria, while the current transmission-blocking vaccines induce antibodies at a low level and thus have no practical value; 4. a multi-stage multi-antigen vaccine that is developed using a composite antigen, such as SP66, which includes an erythrocytic antigen MSP1 peptide and an intermediate replication region of the circumsporozoite protein (CSP), where current clinical experiments show that the multi-stage multi-antigen vaccine exhibits no protective effect; 5. a whole-*Plasmodium* vaccine which is a live attenuated malaria vaccine, including a radiation-attenuated vaccine, a genetically attenuated vaccine, and a drug-attenuated vaccine.

The radiation-attenuated vaccine is generated by irradiating *Anopheles* mosquitoes infected with *Plasmodium* to mutant DNA of sporozoites such that the sporozoites cannot enter erythrocytic stage, thereby achieving attenuation. The sporozoite vaccines obtained using radiation-attenuated *P. falciparum* and *P. vivax* have a protective effect but low protectivity. In addition, radiation attenuation is not controllable and cannot guarantee safety, which limits the application of the radiation-attenuated vaccine.

The drug attenuated vaccine provides immunity by infecting a host with a wild-type *Plasmodium* and killing *Plasmodium* by administering the host with an antimalarial drug. Early experiments verified that the oral administration of chloroquine to a volunteer bit by an *Anopheles* mosquito infected with *P. falciparum* to control erythrocytic infection can induce complete protective effects. However, the volunteer who does not take the antimalarial drug on time after inoculated with *P. falciparum* will suffer from parasitemia and adverse reactions, and may spread malaria after bit by the *Anopheles* mosquito, which has a greater risk and restricts the application of attenuated vaccines.

At present, the genetically attenuated vaccine is mainly to knock out necessary genes in the late liver stage or the pre-erythrocytic stage of *Plasmodium* so that *Plasmodium* cannot enter the erythrocytic stage. Compared with the drug attenuated vaccine, the genetically attenuated vaccine has no risk of spreading malaria and will not cause parasitemia. Moreover, as a whole-*Plasmodium* living vaccine, the genetically attenuated vaccine can induce obvious protective effects and is an excellent malaria vaccine. However, knocking out genes necessary for the development of *Plasmodium* or toxic genes may affect the growth of *Plasmodium* or the expression of surface antigens.

A ubiquitin-proteasome system (UPS) is a non-lysosomal protein degradation pathway in cells.

Ubiquitin is a small molecule globular protein which consists of 76 amino acid residues, is ubiquitous and highly conservative in eukaryotic cells, has a molecular weight of about 8.5 kDa, and can bind to receptor proteins in cells through covalent bonds. Cells can degrade proteins through the UPS pathway, so as to control an expression level of protein produced through constitutive regulation and environmental stimuli. A variety of physiological processes of cells, including cell apoptosis, cell proliferation and differentiation, quality control of endoplasmic reticulum proteins, protein translocation, inflammatory response, antigen presentation, DNA repair, and cellular stress responses are all related to the UPS. In addition, the UPS can degrade abnormal proteins, such as unfolded proteins, damaged proteins, mutated proteins, and incorrectly transcribed proteins. Therefore, the UPS plays an important role in maintaining normal cell functions.

A DHFR degradation domain (DDD) is a regulatory system which regulates a target protein by using the ubiquitin-proteasome system. The DDD regulates the target protein by fusing *E. coli* dihydrofolate reductase (ecDHFR) with the target protein and controlling the addition of a stabilizer. The ecDHFR can be stabilized by trimethoprim (TMP), a DHFR inhibitor. With no TMP added, ecDHFR and the protein fused therewith are labelled with ubiquitin, and recognized and degraded by proteasomes. With TMP added, TMP binds to and stabilizes ecDHFR, so that the protein fused with ecDHFR remains stable and not degraded by ubiquitin, thus the target protein can be expressed normally. The binding of TMP to ecDHFR to stabilize the protein from being degraded is reversible. The addition of TMP can stabilize ecDHFR, and the withdrawal of TMP will cause the degradation of ecDHFR and the protein fused therewith. In addition, the expression level of the target protein can be controlled by controlling the amount of TMP, so it is very convenient to control the expression of the target protein and the expression amount of the target protein through TMP In addition, since the DDD regulatory system controls the expression of the target protein through ubiquitination and degradation, secreted proteins cannot be regulated.

Therefore, there is a need to develop a technology for conditionally regulating the expression of necessary genes of *Plasmodium*. The necessary genes are expressed first to make *Plasmodium* survive, and stopped to be expressed after the immune protection is obtained to achieve attenuation. The regulatory system is required not to express the necessary genes in the absence of a regulatory drug and to express the genes after a regulatory drug is added to make *Plasmodium* survive, thereby avoiding the spread of malaria caused by the surviving *Plasmodium*.

SUMMARY

In view of the defects in the existing art and the actual requirements, the present disclosure provides an attenuation system and use thereof. A regulatory system is adopted to regulate the expression or degradation of an EF1g gene, so as to control the growth of *Plasmodium* and attenuate *Plasmodium*.

To achieve the object, the present disclosure adopts solutions described below.

In a first aspect, the present disclosure provides use of an EF1g gene for attenuating *Plasmodium*.

In the present disclosure, the inventors have found that EF1g (PBANKA 1352000 elongation factor 1-gamma) is a necessary gene of *P. berghei*, and thus a regulatory element is adopted to regulate its expression, so as to control the survival of *Plasmodium* and attenuate *Plasmodium*.

According to the present disclosure, the EF1g gene has a name of "elongation factor 1-gamma", and has a gene identification number of PBANKA 1352000 and a nucleotide sequence as shown in SEQ ID NO. 1, wherein the specific sequence is as follows:

ATGGATTTAAAACTTCTTGGCCCAAAAAATGATATCAGATGTTTGAAGGT

GCAAACAGTTGCTTCTTTTTGTAATATAAAACTAAATATCCCAACATTTG

AAATCGGTATTGATGATAATAAAGATGAATTTATAAAAGAATCGCCAATG

AAAAGACTTCCAGTTTTAATAACACCCCAAGGAAGCTTATTTGAAAGCAA

TGCTATAGGAAAATATTTATGCAGTATAAGAAGTGAACATAATTTATTGG

GAAATGGAATTTTTGAAGAAGGGCAAGTAAATATGTGGGTAGATTTTTGT

ACATTTGAATTAGAAATTCCAGTATGCTGTTATATTAGTAATAAGTTGAA

TGAAAAATCGTTAAAACATATTCAAGATACATTTAGTTGTTTAAATAAAC

ACTTACTATTAAATCAGTATATGGTAGGTAACAACATAACTATTGTTGAT

ATTTTTATGTCTGTAATTATAAATTTTTGTATAAAATCGGGAAAAATGAC

TGAAGCCTTTTTAAAACAATATGGAAACTTATACAGATTATATACAACTA

TAATAAATCAGAAACAATTTAAATATGTTATGGGTTCAGGATCAGCTGTA

AATAATAAAAAACACCTACTCAACCCAAACAGCCAAATAATAAGGAAAA

AAAAAAACCAAAAGAAGATGCAGATGATGATATTAATCTATTTAGTGATG

ATGGACTTAATGAAAAAAAAACAAAAAAGACAAACCCTTTAGATTTATTA

CCTCCATCAAAATTTTCTTTAGATAACTGGAAATATAAATTTAGTAATGA

AAAGGATTTATTAAAAAATGCAATGCCCACATTTTGGGAAACTTATGATA

GTAATGGATTTTCATTATATTATATGAAATATGATAAATTAGAAGATGAA

TGCCAAATATCTTTTGTTGCTTGTAATATGGCTAGTGGGTTTTTACAAAG

GTTAGAAAACAATTTCTCAAAATACTCATTTGCAGTTATATCTGTTTTAG

GGGAAAATAAAAATTATGATATTGAAGGTGTTTGGCTATTTAGAGGTACT

GAAATTCCTTTTGAAATGAAAGACCATCCATCTTTTGAATATCACATTTT

TAAAAAATTAGATATTAATAACAGTAATGATAAAAAACTTGTTGAAGATT

-continued

ATTGGTGTTCAAAAGAAATTATTTCTAATAGACCTGTTTGTGATAGAAAG

GTTTGGAAATGA.

According to the present disclosure, the *Plasmodium* is any one or a combination of at least two of *P. berghei, P. falciparum, P. vivax, P. malariea, P. ovale*, or *P. knowlesi*, preferably *P. berghei*.

In a second aspect, the present disclosure provides a recombinant vector, where the recombinant plasmid includes an EF1g gene.

The present disclosure constructs a vector for achieving knock-in. A Cas9 knock-in vector is constructed to knock a regulatory element together with a reporter gene in a specific gene in a genome of a host cell.

According to the present disclosure, the vector is any one or a combination of at least two of a plasmid vector, a phage vector, or a viral vector, preferably a plasmid vector.

According to the present disclosure, the recombinant vector further includes a regulatory element located upstream of the EF1g gene.

In the present disclosure, the regulatory element can be knocked in a genome of *Plasmodium* through the recombinant vector. The regulatory element is knocked in the upstream of the EF1g gene in the genome, so that the expression of the EF1g gene in the genome can be controlled, and the transcription of the gene or the corresponding protein expressed by the gene can be controlled by a regulatory system.

According to the present disclosure, the regulatory element is any one or a combination of at least two of a dihydrofolate reductase regulatory element (DDD), a tetracycline operon regulatory element, or an FKBP12 regulatory element, preferably a dihydrofolate reductase regulatory element.

In the present disclosure, the inventors have found that when a DDD assembly is used to regulate the necessary gene to control the expression of the necessary gene of *Plasmodium* at a protein expression level so as to control the survival of *Plasmodium*, the DDD has a low background and a large regulatory expression range and is convenient for regulation compared with other regulatory elements.

According to the present disclosure, the dihydrofolate reductase regulatory element has a nucleotide sequence as shown in SEQ ID NO. 2, wherein the specific sequence is as follows:

ATGATCAGTCTGATTGCGGCGTTAGCGGTAGATTATGTTATCGGCATGGA

AAACGCCATGCCGTGGAACCTGCCTGCCGATCTCGCCTGGTTTAAACGCA

ACACCTTAAATAAACCCGTGATTATGGGCCGCCATACCTGGGAATCAATC

GGTCGTCCGTTGCCAGGACGCAAAAATATTATCCTCAGCAGTCAACCGGG

TACGGACGATCGCGTAACGTGGGTGAAGTCGGTGGATGAAGCCATCGCGG

CGTGTGGTGACGTACCAGAAATCATGGTGATTGGCGGCGGTCGCGTTatt

GAACAGTTCTTGCCAAAAGCGCAAAAACTGTATCTGACGCATATCGACGC

AGAAGTGGAAGGCGACACCCATTTCCCGGATTACGAGCCGGATGACTGGG

AATCGGTATTCAGCGAATTCCACGATGCTGATGCGCAGAACTCTCACAGC

TATTGCTTTGAGATTCTGGAGCGGCGG

According to the present disclosure, the recombinant vector further includes a reporter gene located between the regulatory element and the EF1g gene.

In the present disclosure, the reporter gene is inserted, so as to observe the regulatory effect of the regulatory element on the EF1g gene.

According to the present disclosure, the reporter gene is selected from, but not limited to, a reporter protein GFPm3, and other reporter genes are also usable and will not be detailed here. Those skilled in the art can select a suitable reporter gene as needed.

According to the present disclosure, the reporter protein GFPm3 has a nucleotide sequence as shown in SEQ ID NO. 3, wherein the specific sequence is as follows:

Atgagtaaaggagaagaactttcactggagttgtcccaattcttgttga attagatggtgatgttaatgggcacaaattttctgtcagtggagagggtg aaggtgatgcaacatacggaaaacttacccttaaatttatttgcactact ggaaaactacctgttccatggccaacacttgtcactactttcggttatgg tgttcaatgctttgcgagatacccagatcatatgaaacagcatgactttt tcaagagtgccatgcccgaaggttatgtacaggaaagaactatattttc aaagatgacgggaactacaagacacgtgctgaagtcaagtttgaaggtga taccettgttaatagaatcgagttaaaaggtattgattttaaagaagatg gaaacattcttggacacaaattggaatacaactataactcacacaatgta tacatcatggcagacaaacaaaagaatggaatcaaagttaacttcaaaat tagacacaacattgaagatggaagcgttcaactagcagaccattatcaac aaaatactccaattggcgatggccctgtccttttaccagacaaccattac ctgtccacacaatctgccdttcgaaagatcccaacgaaaagagagaccac atggtccttcttgagtttgtaacagctgctgggattacacatggcatgga tgaactatacaaa.

In a third aspect, the present disclosure provides an attenuation system which inserts a regulatory element upstream of an EF1g gene in a genome of *Plasmodium* through the recombinant vector described in the second aspect.

In a fourth aspect, the present disclosure provides a host cell, where a regulatory element is inserted upstream of an EF1g gene in a genome of *Plasmodium* through the recombinant vector described in the second aspect.

According to the present disclosure, the host cell is *Plasmodium*, preferably, any one or a combination of at least two of *P. berghei, P. falciparum, P. vivax, P. malariea, P. ovale*, or *P. knowlesi*, more preferably *P. berghei*.

In a fifth aspect, the present disclosure provides a vaccine including the attenuation system described in the third aspect and/or the host cell described in the fourth aspect.

In a sixth aspect, the present disclosure provides a method for attenuating *Plasmodium*, including:

infecting an animal with the attenuation system described in the third aspect, the host cell described in the fourth aspect, or the vaccine described in the fifth aspect, and controlling the addition of trimethoprim (TMP) to achieve attenuation.

In the present disclosure, the used regulatory drug TMP can control the growth of *Plasmodium*, and can be directly used in human bodies and penetrate the blood-brain barrier and the placental barrier.

In a seventh aspect, the present disclosure provides use of the attenuation system described in the third aspect, the host cell described in the fourth aspect, or the vaccine described in the fifth aspect for preparing a medicament alleviating side effects of *Plasmodium* infection.

Compared with the existing art, the present disclosure has the following beneficial effects:

(1) the present disclosure has found the necessary EF1g gene of *Plasmodium* for the first time and regulated the EF1g gene through a regulatory element to control the expression or degradation of *Plasmodium* EF1g protein, thereby controlling the growth of *Plasmodium* and attenuating *Plasmodium*; and (2) as a new and feasible *Plasmodium* attenuation strategy, the present disclosure adopts the DDD to regulate the EF1g gene accurately and controllably with a good regulatory effect, and the DDD regulatory system has a low background, is convenient for regulation, and controls the growth of *Plasmodium* in conjunction with TMP, and can be directly used in the human body to attenuate *Plasmodium* after the human body is infected with *Plasmodium*.

BRIEF DESCRIPTION OF DRAWINGS

FIG. 8 (A) shows *Plasmodium* infection rates of groups in a TMP withdrawal experiment, and FIG. 8 (B) shows change curves of *Plasmodium* survival rates of the groups in the TMP withdrawal experiment.

DETAILED DESCRIPTION

To further elaborate on the technical means adopted and the effects achieved in the present disclosure, the solutions of the present disclosure are further described below with reference to the drawings and embodiments, but the present disclosure is not limited to the scope of the examples.

Figure 1:
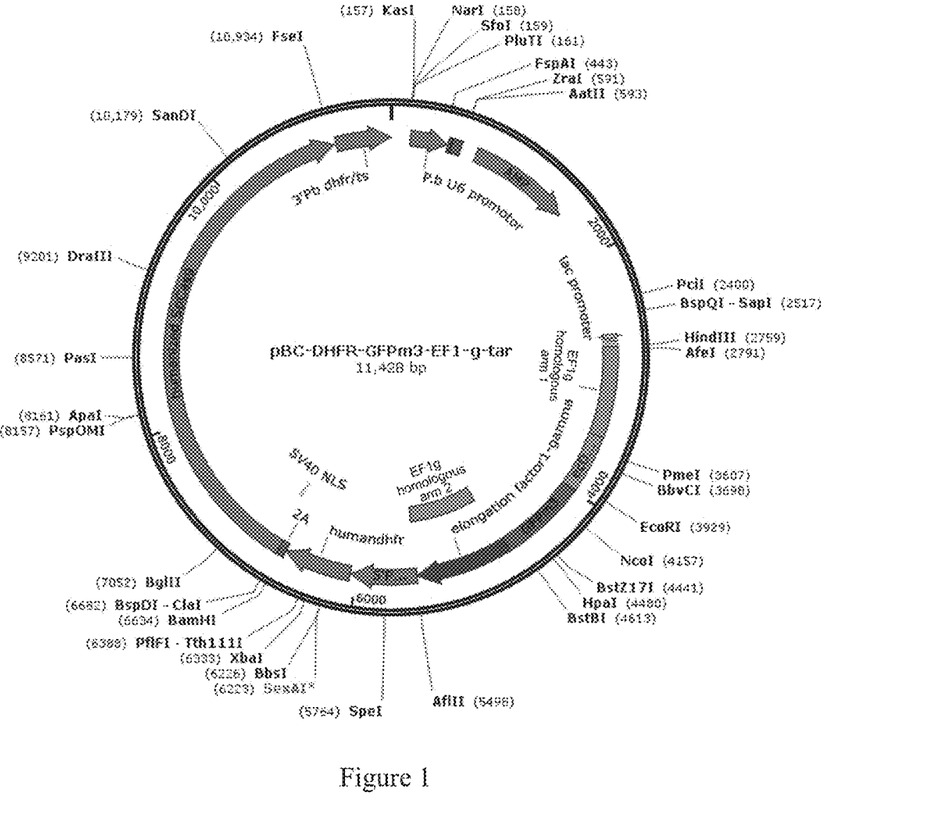
FIG. 1 is a schematic diagram of the pBC-DHFR-GFPm3-EF1g-tar vector.

Example 1 Construction of a Strain that Adopts DDD to Regulate the EF1g Gene in P.bANKA In this example, a Cas9 knock-in vector pBC-DHFR-GFPm3-EF1g-Tar was constructed. The schematic diagram of the vector is shown in FIG. 1. The vector had Amp resistance and contained a gene encoding Cas9 protein and a hDHFR gene conferring *Plasmodium* pyrimethamine resistance which were expressed in tandem, where pbeef1aa was used as a promoter, the Cas9 gene and the hDHFR gene were linked by a 2A peptide, and 3'Pb dhfr/ts was used as a terminator. In addition, the vector further included a fusion expression cassette that included successive sequences of an EF1g homologous arm 1, a regulatory element DHFR, a reporter protein GFP, and an EF1g downstream homologous arm, with pbeef1aa as the promoter and 3'Pb dhfr/ts as the terminator. The vector further included a P.b U6 promoter to express sgRNA.

Homologous arms of the EF1g gene are shown in SEQ ID NO. 4 and SEQ ID NO. 5, and sgRNA primers are shown in SEQ ID NO. 6 and SEQ ID NO. 7. The specific sequences are shown in Table 1.

TABLE 1

| Primer Name | Use | Primer Sequence (5' → 3') |
|---|---|---|
| SEQ ID NO. 4 | EF1g homologous arm 1 | ACTCCTATAGGCTTAATAATTATAAGCGCTATATATATCACAT GCAACTTAAAAAAAAATATGCATATATATAATTTTTCATGATT GCAAAAGAAGTTTGAAATATTTAAAAAATAAAACACATTCC AATTATTTGTCGCTAAATTTTATTTTTAATTAAATATATCGCA CAAAGTATAAACACATATAGTATTTTTCGTGTTAATAAAAT AACAATAGTTGAACTACAAAACGAACTATTTTATTAGTCAAT TAATTTAGGATATTTTTCCTTAAAAAAACTAAATATATATTAT ACCAAATATTTTCCATCATAATTGTAGATTTACTTTTTATTTA AACTAGGGAAAATGGATTTAGTAAGAAAAAAAAAAAAAAAA AAACATATATATTGTATGTTCTAAATATGTTTATAATTTGAGT AAATAAAAATAAAATTTCACATAATATCAGCAATGCATAGTA TAAAAAAAAAACATCAAATTAAAAAATATATATTATTATACA ATTTAAAAAATGAGCATACAACATTTAGTTCATGATATATGC ATAATTATATTATATGTTCATAAAATAATTTTTCTTTATTTTTT TTTCTTAATTTTCATAGAAACTTCTTGGCCCAAAAAATGATAT CAGATGTTTGAAGGTGCAAACAGTTGCTTCTTTTTGTAATATA AAACTAAATATCCCAACATTTGAAATCGGTATTGATGATAAT AAAGATGAATTTATAAAAGAATCGCCA |

TABLE 1-continued

| Primer Name | Use | Primer Sequence (5' → 3') |
|---|---|---|
| SEQ ID NO. 5 | EF1g homologous arm 2 | AATGCTATAGGAAAATATTTATGCAGTATAAGAAGTGAACAT AATTTATTGGGAAATGGAATTTTTGAAGAAGGGCAAGTAAAT ATGTGGGTAGATTTTTGTACATTTGAATTAGAAATTCCAGTAT GCTGTTATATTAGTAATAAGTTGAATGAAAAATCGTTAAAAC ATATTCAAGATACATTTAGTTGTTTAAATAAACACTTACTATT AAATCAGTATATGGTAGGTAACAACATAACTATTGTTGATAT TTTTATGTCTGTAATTATAAATTTTTGTATAAAATCGGGAAAA ATGACTGAAGCCTTTTTAAAACAATATGGAAACTTATACAGA TTATATACAACTATAATAAATCAGAAACAATTTAAATATGTT ATGGGTTCAGGATCAGCTGTAAATAATAAAAAAACACCTACT CAACCCAAACAGCCAAATAATAAGGAAAAAAAAAACCAAA AGAAGATGCAGATGATGATATTAATCTATTTAGTGATGATGG ACTTAATGAAAAAAAACAAAAAGACAAACCCTTTAGATTT ATTACCTCCATCAAAATTTTCTTTAGATAACTGGAAATATAAA TTTAGTAATGAAAAGGATTTATTAAAAAATGCAATGCCCACA TTTTGGGAAACTTATGATAGTAATGGATTTTCATTATATTATA TGAAATATGATAAATTAGAAGATGAATGCCAAATATCTTTTG TTGCTTGTAATATGGCTAGTGGG |
| SEQ ID NO. 6 | EF1-g-tar1-F | tattggagacgCTTTCAAATAAGCTTCCTTGcgtctca |
| SEQ ID NO. 7 | EF1-g-tar1-R | aaactgagacgCAAGGAAGCTTATTTGAAAGcgtctcc |

Plasmid was extracted and linearized, and Pb ANKA was transfected with the plasmid. After electroporation, mixed TMP/pyrimethamine was administrated. The manner for administering to mice infected with *Plasmodium* after electroporation is described below.

Pyrimethamine solution: Pyrimethamine powder was dissolved in DMSO and prepared as a mother liquor with a final concentration of 7 mg/mL (shook and mixed uniformly), and the mother liquor was stored at 4° C. The mother liquor was diluted by a factor of 100 with distilled water, and adjusted to a pH within a range of 3.5 to 5.0 to prepare a working solution which was replaced every seven days.

Administration of mixed TMP/pyrimethamine: 100 mg of TMP was dissolved in 2 mL of DMSO and then added with 1 mL of pyrimethamine mother liquor, and the volume was adjusted to be 100 ml with distilled water, the pH was adjusted to be within a range of 3.5 to 5.0, and the mixed solution was replaced every three days.

Figure 2:
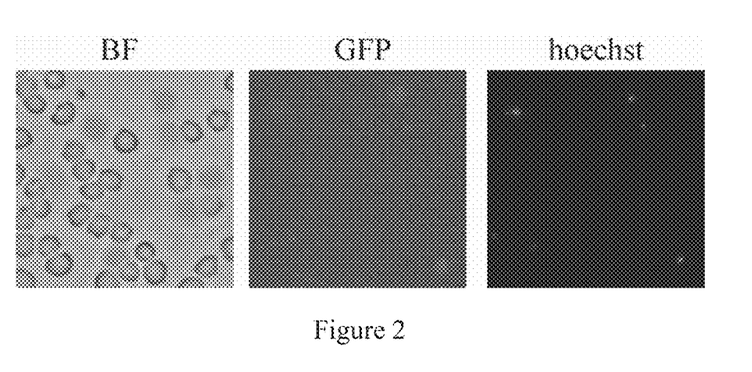
FIG. 2 shows the results of fluorescence observation through a fluorescence microscope, where BF is short for bright field, GFP is short for green fluorescent protein, and hoechst is a dye for labelling a nucleus.
Figure 3:
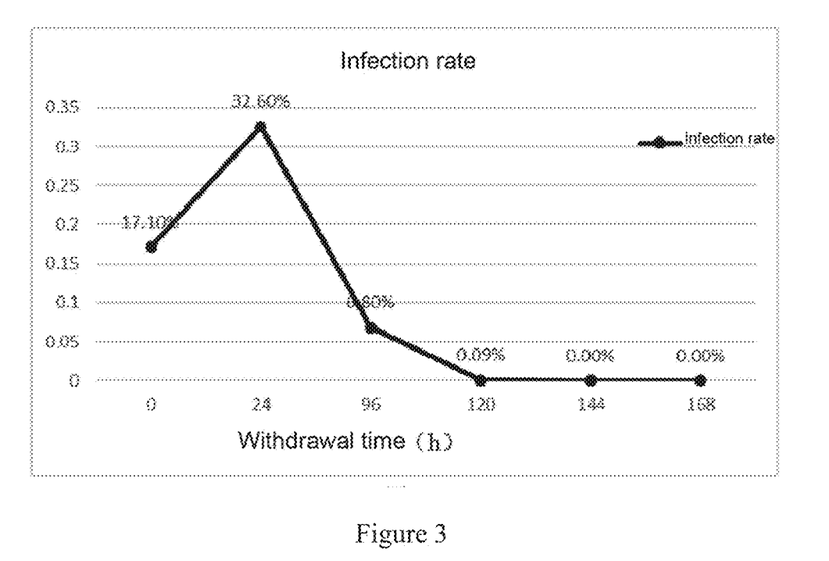
FIG. 3 shows a change curve of a *Plasmodium* infection rate after TMP withdrawal.
Figure 4:
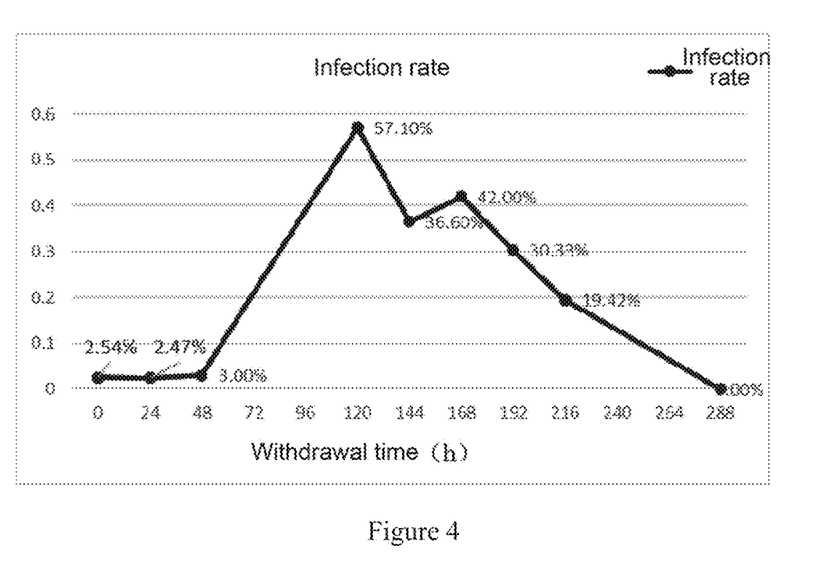
FIG. 4 shows the results of the infection rate of DDD-EF1g strain detected after a second-round of TMP administration followed by withdrawal.

Balb/c (8w, female) mice were inoculated with *P. berghei* electroporated with the plasmid, so that the strain P.bANKA/pBC-DHFR-GFPm3-EF1g-Tar (simply referred to as a DDD-EF1g strain) was successfully obtained. After electroporation, the strain was observed with a fluorescence microscope, and the results are shown in FIG. 2. The strain underwent drug withdrawal experiments (administration of mixed TMP/pyrimethamine, followed by administration of only pyrimethamine once the infection rate exceeded 10%). The change of the infection rate of the strain was observed, and the results are shown in FIG. 3. The transferred second-passage strain underwent TMP withdrawal experiments (administration of mixed TMP/pyrimethamine, followed by administration of only pyrimethamine once *Plasmodium* was found through microscopic examination), and the results are shown in FIG. 4.

It can be seen from FIG. 2 that GFP initiated by the promoter of EF1g has obvious fluorescence whose positions are consistent with those of *Plasmodium* nuclei labelled with Hoechst, and it is determined that GFP was correctly expressed. It can be seen from FIG. 3 that the infection rate decreased from 32.6% to 0.09% after 120 h of withdrawal, and became 0 after 144 h of withdrawal. It can be seen from FIG. 4 that the infection rate increased slightly after 24 h of withdrawal due to residual TMP and decreased to 0 after TMP withdrawal.

It is found from the results of the two experiments that *Plasmodium* can survive only when TMP is administered, which proves that the DDD regulatory system can control the expression of the necessary gene of *Plasmodium* by administering TMP or not to control the survival of *Plasmodium* and adjust the toxicity of *Plasmodium*.

Example 2 Verification of the Effect of DDD in Regulating EF1g Gene in P.bANKA

Figure 5:
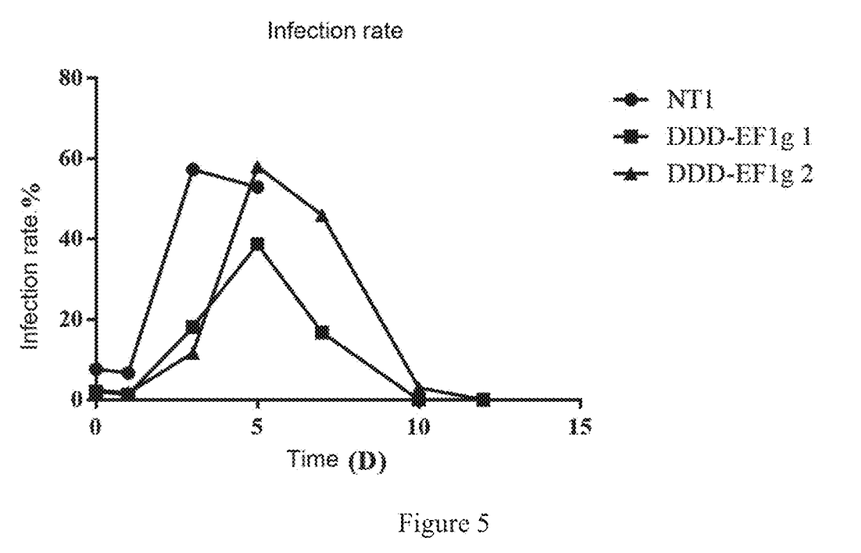
FIG. 5 shows change curves of *Plasmodium* infection rates and survival rates of groups in a TMP withdrawal experiment.

Two Balb/c (8w, female) mice were inoculated with the P.bNAKA/pBC-DHFR-GFPm3-EF1g-Tar strain, and one mouse was inoculated with *P. berghei* whose non-necessary gene NT1 was knocked out by using a CRISPR-Cas9 system as a control group. Mixed TMP/pyrimethamine was initially administrated, and TMP withdrawal experiments were carried out after the *Plasmodium* infection rate exceeded 1%. After TMP withdrawal, blood was collected from mice and smears were prepared to calculate the infection rate. The results are shown in FIG. 5.

It can be seen from FIG. 5 that the mouse in the control group NT1 died 7 days after TMP withdrawal, while the infection rates of all mice in DDD-EF1g group decreased to 0; after TMP withdrawal (administration of mixed TMP/pyrimethamine at first, followed by administration of pyrimethamine after TMP withdrawal), the infection rate of the mouse in the control group NT1 continued increasing and the mouse died 5 days later, while the infection rates of the two mice in DDD-EF1g group decreased to 0.5 days after TMP withdrawal, and the mice survived.

It can be seen that after TMP withdrawal, *Plasmodium* in the mice infected with the DDD-EF1g strain died, indicating that the DDD can regulate the expression of the EF1g gene, control the survival of *Plasmodium*, and attenuate *Plasmodium*.

Example 3 Effect of DDD in Regulating EF1g Gene in P.bANKA

In this example, a Balb/c (8w, female) mouse was inoculated with a DDD-GFP strain constructed by our company (the DDD regulates GFP expression and does not regulate any necessary gene) to verify whether TMP remains after TMP withdrawal. In addition, 6 Balb/c (8w, female) mice were inoculated with the DDD-EF1g strain. The administration method for mice is shown in Table 2.

TABLE 2

Administration of mice in groups

| Strain | DDD-GFP | DDD-EF1g | |
|---|---|---|---|
| Group No. | G1 | G2 | G3 |
| Administration | Administration of TMP followed by withdrawal | Continuous administration of TMP | Administration of TMP followed by withdrawal |
| Number of mice | 1 | 2 | 2 |
| Purpose | Determine whether TMP remains after withdrawal | Determine an effect of TMP | Determine whether EF1g is necessary |
| Administration | Description (administration by drinking water with a pH of 3.5 to 5) | | |
| Administration of TMP followed by withdrawal | 1 mg of TMP and 0.07 mg of pyrimethamine/mL of water→infection rate reaching 1%→0.07 mg of pyrimethamine/mL of water | | |
| Continuous administration of TMP | 1 mg of TMP and 0.07 mg of pyrimethamine/mL of water | | |

Figure 6:
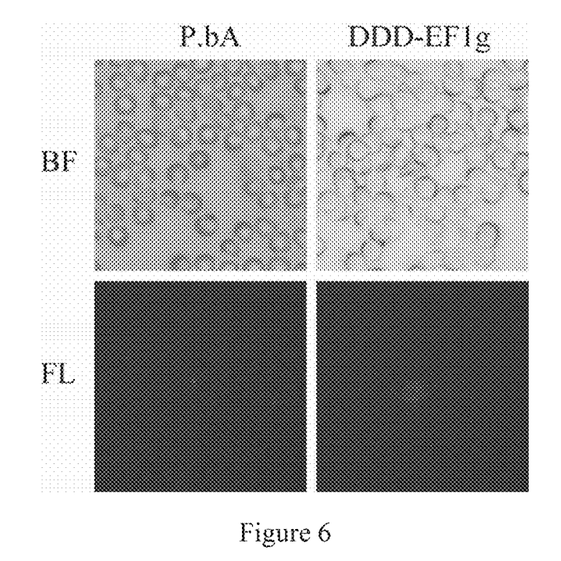
FIG. 6 shows the results of fluorescence of G1 and a wild-type P.b A strain detected through a fluorescence microscope, where BF is for bright field, and FL demotes results under a fluorescent light.
Figure 7:
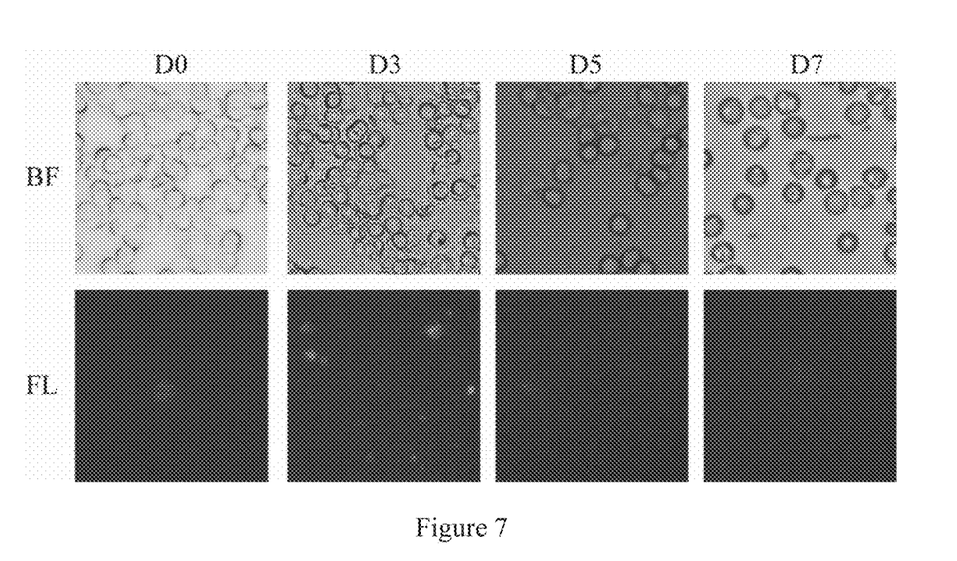
FIG. 7 shows the results of fluorescence of G1 detected through a fluorescence microscope after TMP withdrawal, where BF is for bright field, FL demotes results under a fluorescent light, and D denotes the number of days after TMP withdrawal.

After the *Plasmodium* infection rate exceeded 1%, TMP was withdrawn for groups G1 and G3. Before TMP withdrawal, GFP fluorescence of the DDD-EF1g strain was observed, and the results are shown in FIG. 6. After the TMP withdrawal, the fluorescence of G1 was observed, and the results are shown in FIG. 7. The results of the infection rate and the survival rate of the mice in all groups are shown in FIG. 8 (A) and FIG. 8 (B).

It can be seen from FIG. 6 that the administration of TMP can stimulate the fluorescence of the strain in G1 before TMP withdrawal, which proves that TMP works. It can be seen from FIG. 7 that the fluorescence of the DDD-GFP strain in G1 increased on the third day after withdrawal, and no GFP fluorescence was detected on the fifth day and the seventh day after withdrawal. It is considered that TMP remained in the mouse on the third day after withdrawal, and TMP was consumed on the fifth day after withdrawal.

Figure 8A:
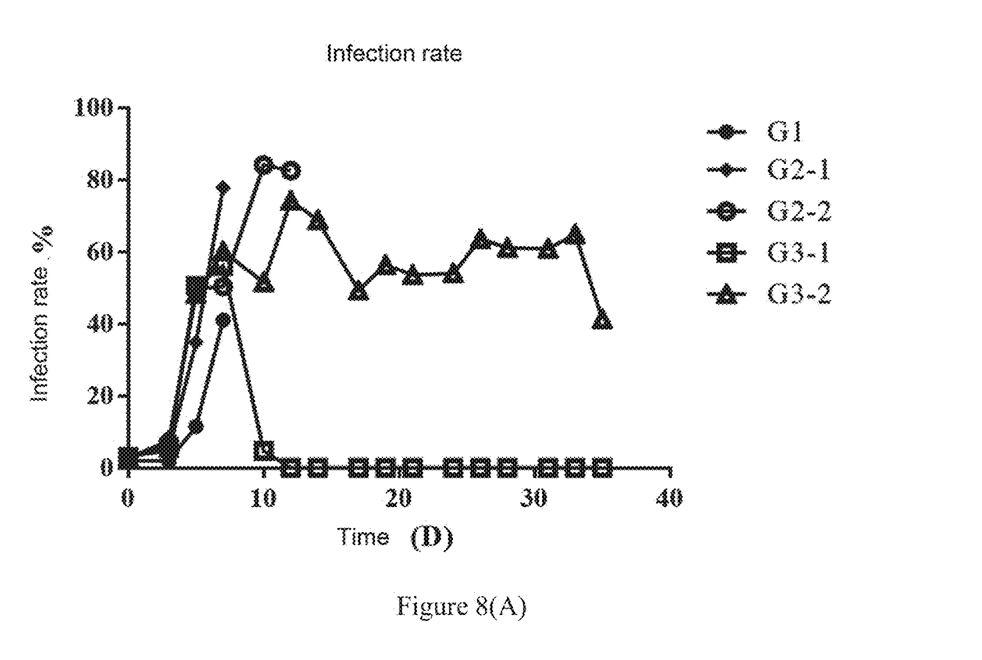
Figure 8B:
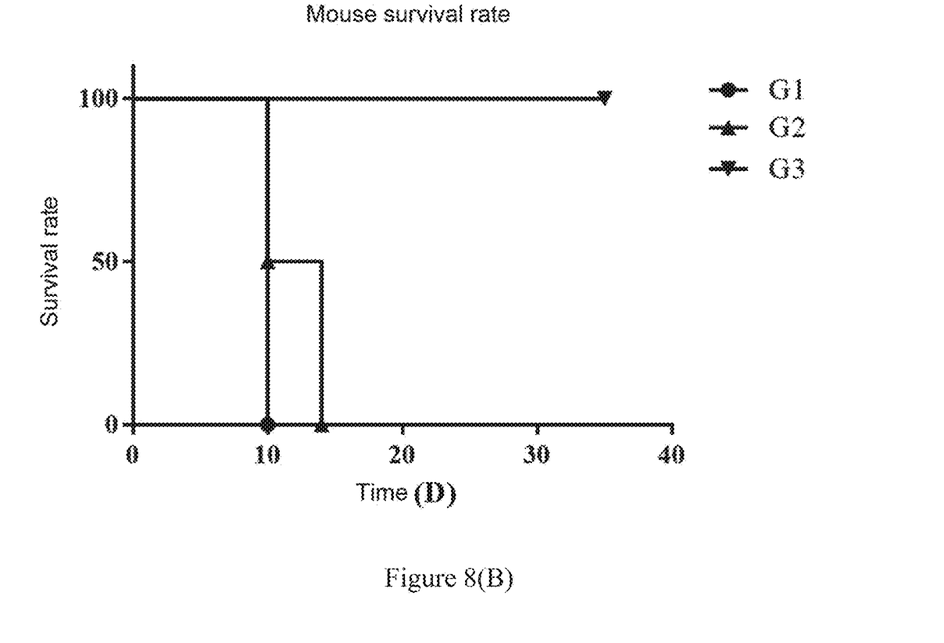

It can be seen from FIG. 8 (A) and FIG. 8 (B) that except those in G3, all mice in G1 and G2 died, the infection rate of one of the two mice in G3 decreased to 0, and the infection rate of the other mouse remained 50% to 60%, but no mice died; all mice in G2 died, which proved that the continuous administration of TMP cannot cause the death of the DDD-EF1g strain, and the withdrawal of TMP is a key factor affecting the death of the DDD-EF1 g strain; the death of the mouse in G1 proved that the strain where the DDD regulated a non-necessary gene would not die after withdrawal of TMP following TMP administration, and only the strain whose necessary gene was regulated by the DDD was affected by regulation of TMP administration.

To conclude, this example proves that the growth of the DDD-EF1g strain is affected by regulating TMP, and that the regulation of DDD in the expression of the EF1g gene of *Plasmodium* is an effective means to achieve the survival of *Plasmodium* and the attenuation of *Plasmodium* through external regulation.

Figure 9:
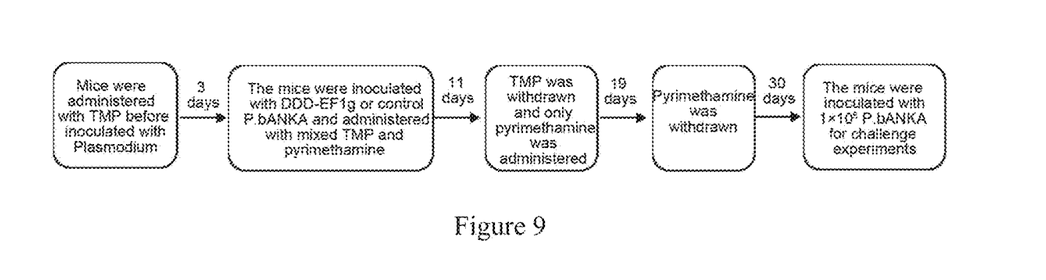
FIG. 9 is a schematic diagram of a *Plasmodium* inoculation and administration process in a challenge experiment.

Example 4 Verification of the Effect of a DDD-Regulated Attenuated Vaccine in Preventing *Plasmodium* Infection Balb/c (female, 8w) mice were inoculated with the P.bNAKA/pBC-DHFR-GFPm3-EF1g-Tar strain constructed in Example 1 (experimental group) and a wild-type P.bANKA strain (control group). The mice were administrated with TMP (1 mg of TMP/mL of water, administration by drinking water) for 3 days before inoculated with *Plasmodium* (8 mice in the experimental group and 6 mice in the control group), and then administered with TMP/pyrimethamine (1 mg of TMP and 0.07 mg of pyrimethamine/mL of water with a pH of 3.5 to 5, administration by drinking water). After the *Plasmodium* infection rate exceeded 1%, TMP was withdrawn (0.07 mg of pyrimethamine/mL of water with a pH of 3.5 to 5, administration by drinking water). The *Plasmodium* infection rate of the experimental group decreased to 0. The mice were inoculated with $1 \times 10^5$ P.bANKA one month later for challenge experiments. The mice in the experimental group and the control group were administered and inoculated according to the process in FIG. 9. The change curves of the infection rates of the mice in the experimental group and the control group are shown in FIGS. 10 to 12.

Figure 10:
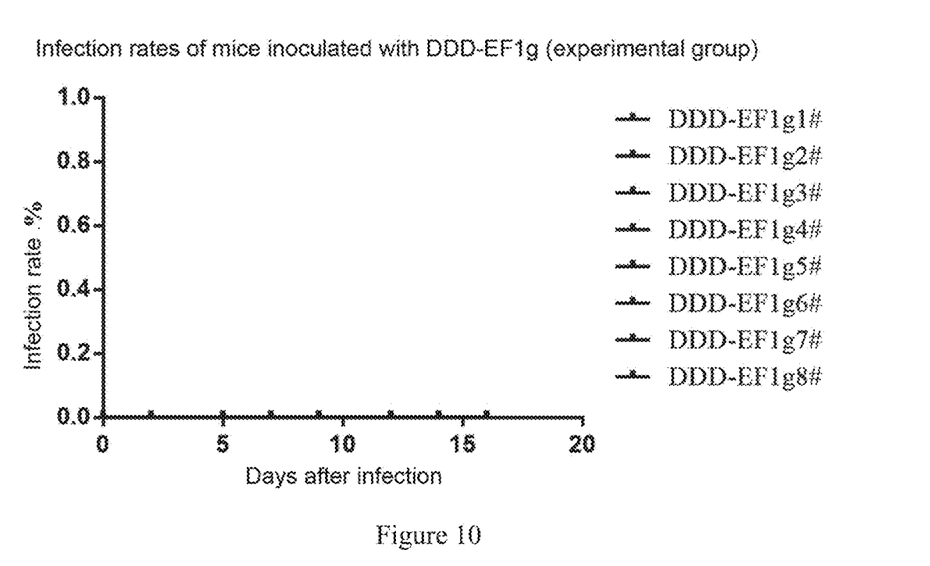
FIG. 10 shows change curves of infection rates of mice inoculated with DDD-EF1g (experimental group).
Figure 11:
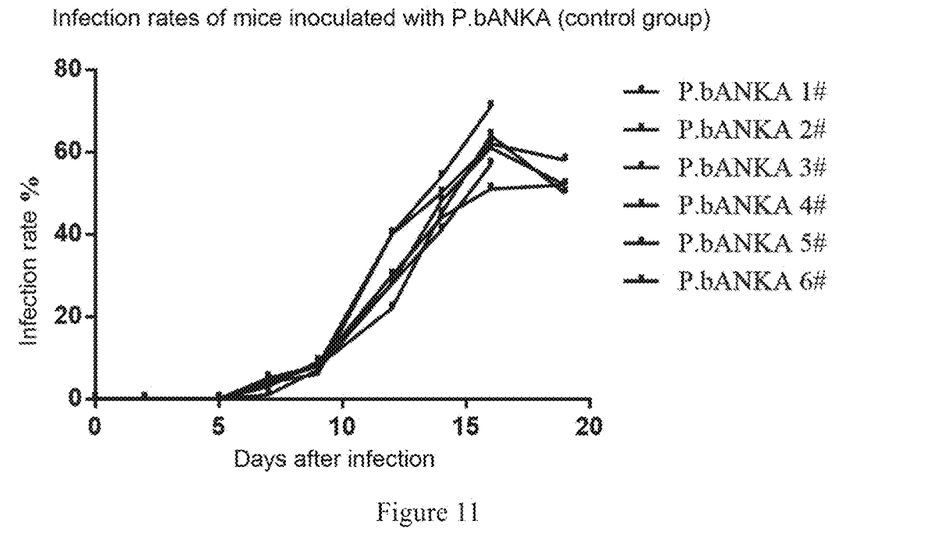
FIG. 11 shows change curves of infection rates of mice inoculated with P.b ANKA (control group).
Figure 12:
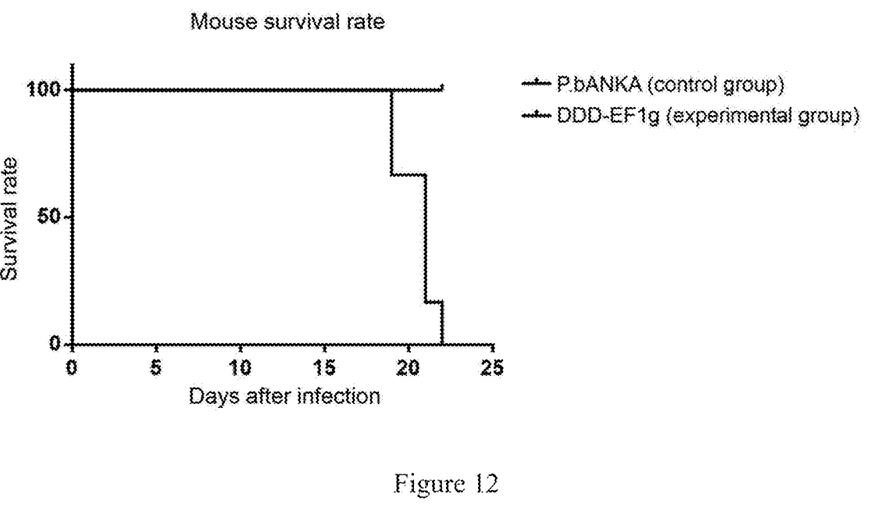
FIG. 12 shows survival rates of mice after a *Plasmodium* challenge.

It can be seen from FIGS. 10 to 12 that *Plasmodium* in all mice in the experimental group died and the infection rate decreased to 0 after TMP withdrawal. 8 mice in the experimental group and the mice in the control group were inoculated with $1 \times 10^5$ P.bANKA, and the *Plasmodium* infection rates were calculated. After inoculation with $1 \times 10^5$ P.bANKA, no growth of *Plasmodium* was observed in the mice in the experimental group and all the mice survived (FIGS. 10 and 12), while the mice in the control group all died from a high infection rate 22 days after inoculation (FIGS. 11 and 12) and all showed *Plasmodium* growth. It is proved that the *Plasmodium* vaccine where the necessary gene is controlled using the DDD regulatory system has obvious preventive and protective effects, and can effectively prevent the vaccinated mice from being infected by *Plasmodium* and is valuable for serving as a *Plasmodium* vaccine.

To conclude, as a new and feasible *Plasmodium* attenuation strategy, the present disclosure adopts the DDD to regulate the EF1g gene accurately and controllably with a good regulatory effect, and the DDD regulatory system has a low background, is convenient for regulation, and controls the growth of *Plasmodium* in conjunction with TMP, and can be directly used in the human body to attenuate *Plasmodium* after the human body is infected with *Plasmodium*.

The applicant has stated that although the detailed method of the present disclosure is described through the examples described above, the present disclosure is not limited to the detailed method described above, which means that the implementation of the present disclosure does not necessarily depend on the detailed method described above. It should be apparent to those skilled in the art that any improvements made to the present disclosure, equivalent replacements of various raw materials of the product, the addition of adjuvant ingredients, and the selection of specific manners, etc. in the present disclosure all fall within the protection scope and the scope of disclosure of the present disclosure.

What is claimed is:

1. An attenuation system, which comprises a modified genome of *Plasmodium* with an exogenous nucleotide sequence encoding a regulatory element upstream of the EF1g gene in a genome of *Plasmodium*, wherein said exogenous nucleotide sequence is as shown in SEQ. ID NO. 2, and wherein the EF1g gene has the nucleotide sequence as shown in SEQ ID NO. 1.

2. A host cell of *Plasmodium*, which comprises the attenuation system according to claim 1.

3. The host cell according to claim 2, wherein the host cell is selected from the group consisting of *Plasmodium berghei, Plasmodium falciparum, Plasmodium vivax, Plasmodium malariea, Plasmodium ovale*, and *Plasmodium knowlesi*.

4. A vaccine, comprising the attenuation system according to claim 1 or the host cell according to claim 2.

5. A method for attenuating *Plasmodium*, comprising:
    infecting an animal with the attenuation system according to claim 1, and controlling the addition of trimethoprim (TMP) to achieve attenuation.

6. The method according to claim 5, wherein the *Plasmodium* is any one or a combination of at least two of *Plasmodium berghei, Plasmodium falciparum, Plasmodium vivax, Plasmodium malariea, Plasmodium ovale*, or *Plasmodium knowlesi*, preferably *Plasmodium berghei*.

* * * * *